United States Patent [19]

Mizuta

[11] Patent Number: 4,950,068
[45] Date of Patent: Aug. 21, 1990

[54] OPHTHALMIC DISEASE DETECTION APPARATUS

[75] Inventor: Susumu Mizuta, Hino, Japan
[73] Assignee: Kowa Company Ltd., Japan
[21] Appl. No.: 216,394
[22] Filed: Jul. 7, 1988
[30] Foreign Application Priority Data Jul. 14, 1987 [JP] Japan .................................. 62-173990

[51] Int. Cl.⁵ ........................... A61B 3/14; A61B 3/10
[52] U.S. Cl. ..................................... 351/208; 351/221
[58] Field of Search ............... 351/205, 214, 221, 208; 128/303.1

[56] References Cited

U.S. PATENT DOCUMENTS 4,213,678 7/1980 Pomerantzeff ...................... 351/221

*Primary Examiner*—Rodney B. Bovernick
*Attorney, Agent, or Firm*—Bruce L. Adams; Van C. Wilks

[57] ABSTRACT

An apparatus for detecting ophthalmic diseases in a patient's eye includes light projection system for projecting a laser beam at a spot in the eye. The light scattered from the eye is photoelectrically detected and converted into an electrical signal which is subsequently used to determine the protein concentration essential to ophthalmic disease detection. A monitor is provided in the light projection system for monitoring light scattered from the cornea of the eye on which the laser beam is projected, and for monitoring a virtual image which is formed by the cornea surface from light scattered at the exit window of the light projection system to correctly position and align the apparatus in order to ensure accurate protein concentration measurements.

11 Claims, 3 Drawing Sheets

OPHTHALMIC DISEASE DETECTION APPARATUS

BACKGROUND OF THE INVENTION

1. Field of the Invention

This invention relates to an apparatus for detecting ophthalmic diseases in a patient's eye, and more particularly to an improvement in the alignment capability of an apparatus used in detecting ophthalmic diseases in which laser light is radiated via an optical system at one spot in the camera oculi of the patient's eye, particularly in the anterior chamber thereof, and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of ciliary body, iris, and the front surface of the crystalline lens, while the camera oculi posterior is defined by a space surrounded by the rear surface of the iris, inner surface of the ciliary body, and front surface of the crystalline lens. The camera oculi is filled with transparent humor aqueous, which has chemical and physical characteristics different from lymphatic liquid and is closely related to the metabolism of the cornea or crystalline lens. The humor aqueous contains proteins which increase causing the camera oculi to be turbid when it becomes inflamed.

In this respect, the measurement of protein concentration in the camera oculi of the patient's eye is of great importance in determining whether the camera oculi is inflamed, that is, whether a blood-aqueous barrier is functioning normally or not.

To measure the protein concentration in the camera oculi, a slit lamp microscope is very often used to determine the turbidity by grading via naked eyes. This is, however, disadvantageous because the diagnosis depends upon the judgement of the person who performs the measurement.

On the other hand, a photographic measuring method has been developed to make a quantitative measurement of the protein concentration. This method is, however, too complicated to analyze, thus making it very difficult to apply in a clinical examination.

To overcome this problem, an apparatus for detecting ophthalmic diseases has been proposed which includes means for focusing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laying-open No. 120834/87.

In order to increase the reliability of the measured data obtained using this type of ophthalmic disease detection apparatus, it is necessary that the measurements are always precisely made on the same part of the eye, which in, turn requires prior positional alignment of the patient's eye with the laser beam projector, and light-receiving means.

To achieve this type of alignment, conventional ophthalmic disease detection apparatuses have been provided with special index means. This makes the apparatus complex, however, because such means requires the use of an optical alignment system and the like, raising the manufacturing cost of the overall apparatus.

SUMMARY OF THE INVENTION

In view of the foregoing, it is an object of the present invention to provide an ophthalmic disease detection apparatus in which the positional alignment process is simplified.

Another object of the present invention is to provide an ophthalmic disease detection apparatus which enables the protein concentration in a patient's eye to be measured with ease and precision.

In an apparatus for detecting ophthalmic diseases in a patient's eye in accordance with the present invention, a laser beam is projected at a selected spot in the patient's eye and light scattered therefrom is received on a photoelectrical converter for conversion into an electrical signal. The apparatus comprises a laser source for producing a laser beam, a laser beam projector for projecting the laser beam, means for focusing the laser beam at a selected spot in the patient's eye, and means provided in the laser beam projector for monitoring light scattered from the cornea of the patient's eye on which the laser beam is projected and a virtual image which is formed by the cornea surface from light scattered at the exit window of the laser beam. The apparatus is positionally aligned relative to the patient in such a manner that the virtual image and the scattered light from the cornea take predetermined positions on the monitoring means.

In the apparatus according to the present invention, light scattered from the cornea of a patient's eye on which a laser beam is projected by a laser beam projector, and a virtual image which is formed by the cornea surface from light scattered at the exit window of the laser beam, can be monitored by monitoring means provided in the laser beam projector. Since the virtual image moves in accordance with the movement of the laser beam projector but the scattered light image does not move, by monitoring these images it is possible to positionally align the apparatus with respect to the eye being examined.

In a preferred embodiment, a polarizing beam splitter or semitransparent mirror is provided behind the exit window to guide the light scattered from the cornea of the patient's eye and the virtual image formed by the cornea surface to the monitoring means.

Preferably, the monitoring means includes a CCD camera for picking up the light scattered from the cornea of the patient's eye and the virtual image formed by the cornea surface and a monitor screen with markings therefor.

Alternatively, the monitoring means includes a monitor screen provided with line sensors to detect the light scattered from the cornea of the patient's eye and the virtual image formed by the cornea surface.

BRIEF DESCRIPTION OF THE DRAWINGS

The objects and features of the present invention will become more apparent from the accompanying drawings and the following detailed description of the invention.

DETAILED DESCRIPTION OF THE PREFERRED EMBODIMENTS

The invention will now be described in detail with reference to the drawings.

Figure 1:
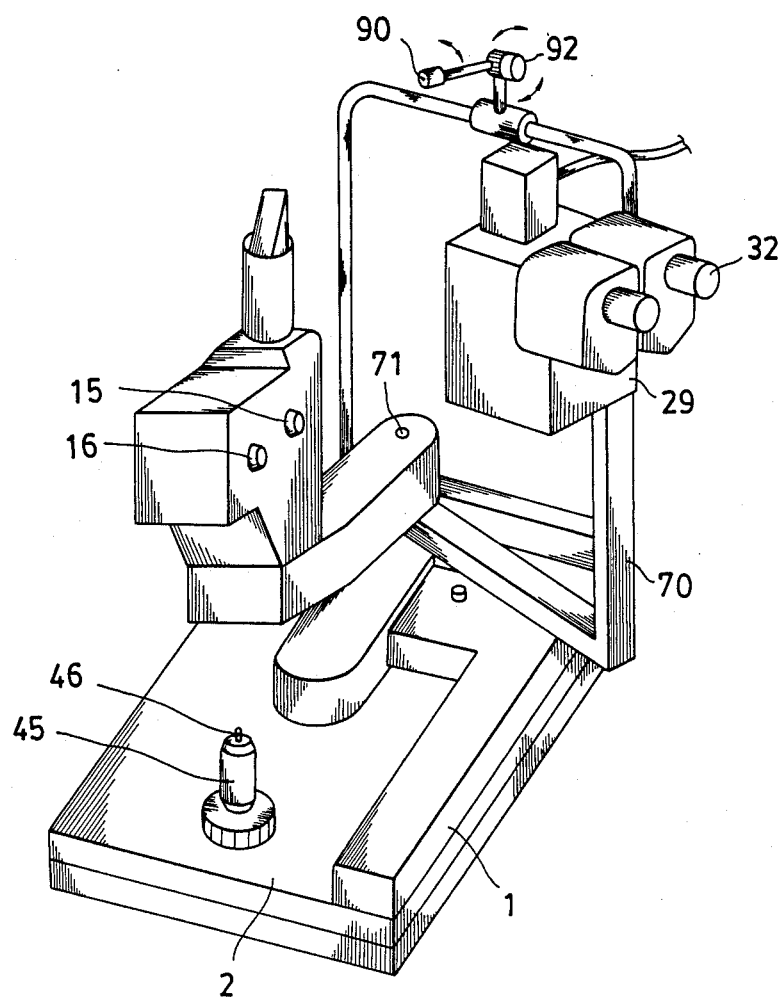
FIG. 1 is a perspective view of an apparatus according to the present invention.
Figure 2:
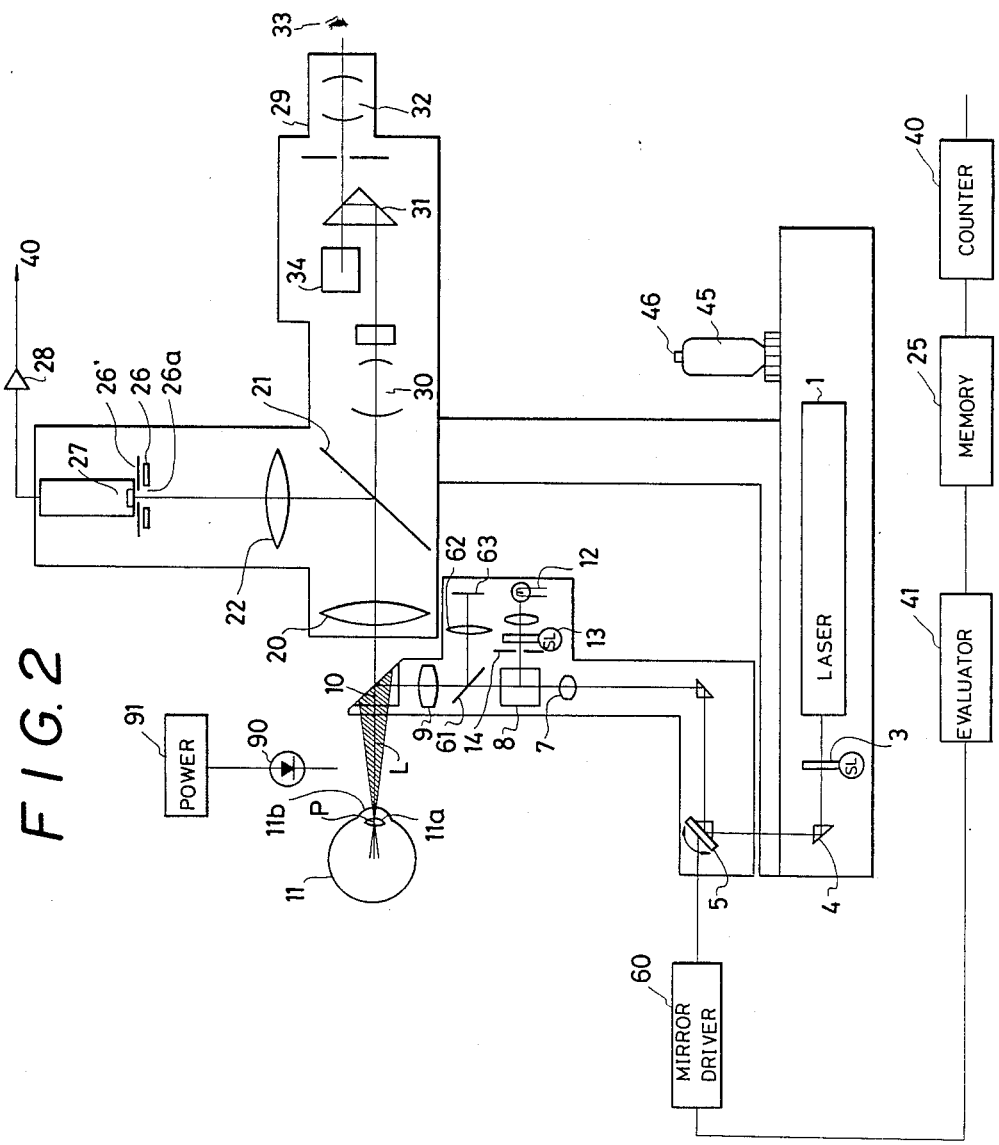
FIG. 2 is a drawing showing the arrangement of the optical system of the apparatus.

In FIGS. 1 and 2 which show an arrangement of the ophthalmic disease detection apparatus according to the present invention, reference numeral 1 denotes a laser light source such as, for example, a helium-neon or argon laser source. The laser light source 1 is disposed on a stand 2. Light from the laser light source 1 is passed through a laser beam filter 3, a prism 4, a swingable mirror 5, a prism 6, a lens 7, a beam splitter 8, a semitransparent mirror (or a polarized light beam splitter) 61, a lens 9 and a prism 10 and converges on an eye under examination 11 at a spot in the anterior chamber 11a thereof.

The laser beam projector is provided with a slit light source 12. Light from the slit light source 12 passes via a slit light shutter 13 and a slit 14 and goes via the beam splitter 8, the prism 6, the lens 9 and the prism 10 to form a slit image in the anterior chamber 11a. With the light from the laser light source being converged to a spot, this slit image is for illuminating the surrounding area to confirm the position of the spot of converged light.

The width of the slit 14 can be adjusted by an adjusting knob 15 and the length of the slit 14 can be switched by a switching knob 16.

A portion of the laser light scattered from the measuring spot in the anterior chamber 11a passes through an objective lens 20 of a light-receiving means 29 and is split by a semitransparent mirror or a beam splitter 21. One part of the light thus split passes through a lens 22, a mask 26 provided with a slit 26a, and a shutter 26' and impinges on a photomultiplier 27 used as the photoelectric converter. The other part of the scattered light split by the beam splitter 21 passes via a lens 30 and prisms 31 and 34 to an eyepiece 32 by means of which an examiner 33 can carry out observations.

The output from the photomultiplier 27 is passed through an amplifier 28, and is then input to a counter 40 which counts the intensity of the scattered light detected by the photomultiplier as numbers of pulses per unit time period. The output of the counter 40, i.e., the number of samplings or the total pulse count, is stored in a memory 25 allocated for each unit time period. The data stored in the memory 25 is processed by an evaluating device 41 which, as explained below, computes the protein concentration in the anterior chamber.

Under the control of the evaluating device 41, the mirror 5 is caused to swing by means of a mirror drive circuit 60, causing the laser beam to scan, thereby moving a spot of laser light within the anterior chamber.

The light-receiving means 29 is affixed to a support 70. The support 70 and the laser beam projector are affixed so that they can rotate, with respect to each other, about a shaft 71 so as to allow the angle between the optical axes of the laser beam projector and the light-receiving means to be adjusted to a required setting. In this preferred embodiment this angle is set to be approximately 90 degrees.

Figure 3:
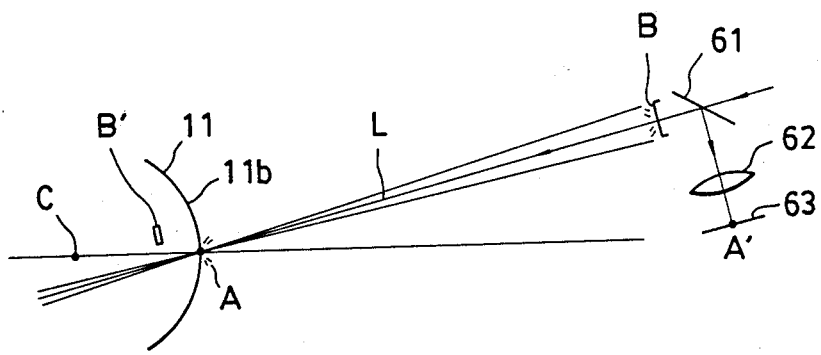
FIGS. 3 and 4 are drawings showing the arrangement of embodiments of the optical system of the apparatus with another optical alignment system.

Also, the laser beam projector is provided with a light-receiving screen or visual indicating means 63, a lens 62 and the semitransparent mirror (polarized light beam splitter) 61. The screen 63 serves to monitor scattered light A from the cornea of the eye at the point of entry of the projected laser beam, and a virtual image B' (see FIG. 3) which is formed by the corneal surface 11b from light scattered at the movable exit window B of the laser beam, for positional alignment of the apparatus relative to the patient's eye.

In accordance with this invention, an eye fixation light 90 comprising a light-emitting diode or the like powered by electricity supplied from a power source 91 is disposed at a position that permits the examiner to fix the patient's eye. The light selected for the eye fixation light 90 is of a different color than the light of the laser light source 1. For example, when the light from the laser light source is red, a green light is selected. The eye fixation light 90 can be turned in the direction indicated by the arrow by means of a link mechanism 92 to enable it to be adjusted so that it is always optimally positioned with respect to the eye being examined.

Provided on the base 2 is an input means, such as a joystick 45 equipped with a push-button 46, and this can be operated to insert the laser filter 3, the slit light shutter 13 and the photomultiplier shutter 26' into, or out of, the optical system concerned.

The operation of the apparatus will now be described. In conducting the measurement, the slit light source 12 is first activated and, via the beam splitter 8, the semitransparent mirror 61, the lens 9 and the prism 10, an image of the slit 14 is formed on a part of the anterior chamber 11a that includes the measuring point P. Following this, light from the laser light source 1 is converged on the measuring point P via the said optical system.

Prior to the measurement the apparatus is first aligned. The scattered light A from the corneal surface 11b of the eye at the point of entry of the projected laser beam, and the virtual image B' which is formed by the corneal surface 11b from light scattered at the exit window B of the laser beam are simultaneously monitored for positional alignment of the apparatus.

The laser beam impinging on the eye produces the scattered light A at the corneal surface 11b. The scattered light is monitored using the same optical axis L as that of the laser beam projector. The light is passed through the laser beam exit window B, the semitransparent mirror 61 to split the optical axis, to the image-formation lens 62 and form an image at the light-receiving screen 63 for alignment purposes. By fixing the distance between the image-formation lens 62 and the light-receiving screen 63, in accordance with image-formation formulae, and by focusing the scattered light image A' on the surface of the light-receiving screen 63 it becomes possible to determine the distance from the laser beam exit window B to the corneal surface 11b.

Figure 5:
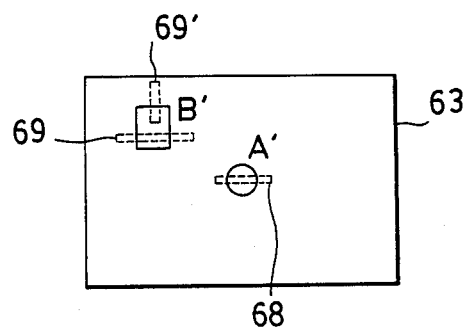
FIG. 5 is an explanatory drawing illustrating the image on a light-receiving screen.

Also, in accordance with curved surface image formation formulae, corneal reflection of the scattered light from the laser beam exit window B forms a virtual image B' over a line linking the corneal center of curvature C with the axis of the laser beam exit window B. The virtual image B' and the scattered light image A' are monitored on the light-receiving screen, as illustrated by FIG. 5. As the scattered light image A' is made in focus, laser beam exit window B is observed as an out-of-focus virtual image B'. Because image A' is monitored using the same optical axis as that of the laser beam projector, there is no movement of the image A' on the light-receiving screen. Therefore, having the center of the virtual image B' at a predetermined position above the light-receiving screen 63 ensures that the laser beam projection position will be at a plane perpendicular to the optical axis of the projected beam. Thus, this determines the three-dimensional components of the measurement location, enabling ophthalmic measurements to be carried out with a high degree of precision.

Measurement is started following the above alignment.

A portion of the light from the measuring point P is simultaneously directed by the beam splitter 21 to the examiner 33 for observation and through the lens 22, a prism 23 and the mask 26 to impinge on the photomultiplier 27.

The mirror 5 is driven to swing in the direction indicated by the arrow by means of the mirror drive circuit 60, causing the part to be measured to be scanned by the laser beam.

The photomultiplier 27 receives the incident scattered laser light via the slit 26a, detects the intensity of the light that has been scattered by protein particles in the anterior chamber 11a and converts this information into a corresponding series of pulses which are counted by the counter 40 as numbers of pulses per unit time period. The count values are then stored in a memory 25 allocated for each unit time period. The data stored in the memory 25 is processed by the evaluating device 41 to compute the concentration of protein in the anterior chamber.

Figure 4:
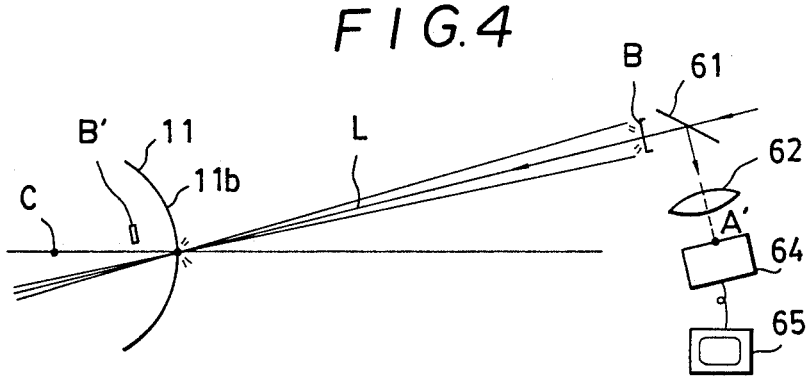
Figure 6:
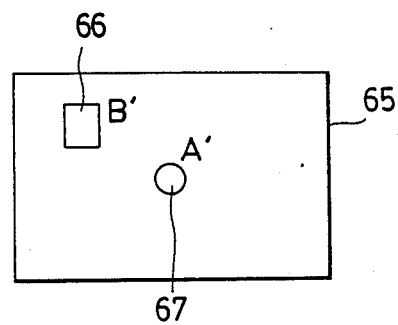
FIG. 6 is an explanatory drawing illustrating the image on a monitor screen.

FIG. 4 illustrates another embodiment of the present invention. In this embodiment, a CCD camera 64 replaces the light-receiving screen 63 of the previous embodiment, which displays on the monitor screen 65 the scattered-light image A' and the virtual image B' as shown in FIG. 6. For alignment purposes image A' does not move even when the optical system is moved, so alignment can be facilitated by adjusting the CCD camera 64 to display the image A' at a predetermined position on the monitor screen 65 (indicated by first indicating means, 67) and by providing an index or second indicating means 66 at an image B' as a target value on the monitor screen. For example, if a joystick or the like is used to move the optical system to focus the scattered light image A' and with the image A' in focus the optical system is gradually moved to set the virtual image B' to the position of the index 66, precise positioning of the projected laser beam becomes possible.

With this method, although it is not illustrated, positioning can be carried out automatically by processing image information from the area sensor of the CCD camera and providing an autofocus mechanism for the image A' and a moving mechanism for the image B'.

In another embodiment, as shown by the broken line portions in FIG. 5, an image focusing line sensor or first detecting means 68 and image position detection line sensors 69, 69' or second detecting means are provided on the light-receiving screen 63. Image focusing line sensor 68 is positioned in the vicinity of the positioning detection optical axis, part of which coincides with the axis of laser beam projection, so that it includes the image A'. When the peak width of information from the line sensor 68 that is passed through a differential filter, for example, is the same or less than a predetermined value, it is considered to be in a state of focus.

As shown in FIG. 5, the line sensors 69, 69' are disposed substantially at right-angles to each other. When the optical system is moved so that each of the line sensors at a maximum value moves to its predetermined position, the center of the image B' is at the predetermined position. As a result, three-dimensional positioning can be performed.

With this method, while not illustrated, the positioning state can be indicated by means of LEDs or the like disposed within the visual field of a microscope provided in the optical observation system for monitoring the measurement position, or it can be done manually. Positioning can also be done automatically in the same way as in the above first method, utilizing information from the line sensors.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed:

1. An apparatus for detecting ophthalmic diseases in a patient's eye, in which a laser beam is projected at a selected spot in the patient's eye and light scattered therefrom is received on a photoelectric converter for conversion into an electrical signal, comprising:

a laser source for producing a laser beam;
a laser beam projector for projecting the laser beam;
means for focusing the laser beam at a selected spot in the patient's eye; and
means provided in the laser beam projector for monitoring light scattered from the cornea surface of the patient's eye on which the laser beam is projected, and a virtual image which is formed by the cornea surface from light scattered at the exit window of the laser beam;
wherein the monitoring means is provided with a monitor screen and disposed with its optical axis the same as that of the laser beam projector so that the monitoring means receives an image of the light scattered from the cornea surface at a predetermined position on the monitor screen irrespective of the alignment of the apparatus relative to the patient's eye, while receiving the virtual image at a position on the monitor screen depending on its alignment relative thereto.

2. An apparatus as set forth in claim 1; wherein a polarizing beam splitter or semitransparent mirror is provided behind the exit window to guide the light scattered from the cornea of the patient's eye and the virtual image formed by the cornea surface to the monitor screen.

3. An apparatus as set forth in claim 1; wherein the monitoring means includes a CCD camera for picking up the light scattered from the cornea surface of the patient's eye and the virtual image formed by the cornea surface, and the monitor screen has markings formed thereon.

4. An apparatus as set forth in claim 1; wherein the monitor screen is provided with line sensors to detect the light scattered from the cornea surface of the patient's eye and the virtual image formed by the cornea surface.

5. In an apparatus for examining particles in a patient's eye in which a laser beam is projected at a spot in the patient's eye and light scattered therefrom is received by light converting means for converting the scattered light into an electrical signal to be evaluated in order to detect for ophthalmic diseases:

light projecting means, a part of which is movable, for projecting the laser beam at a selected spot in the patient's eye; and monitoring means for monitoring both the position of a virtual image formed by light scattered from said movable part of said light projecting means, the virtual image being movable in response to movement of said movable part of said light projecting means, and the position of the scattered light image from the selected spot in the patient's eye so that the virtual image can be moved relative to the scattered light image by movement of said movable part of said light projecting means to place the two images in predetermined positions to thereby effect alignment of said light projecting means relative to the patient's eye.

6. An apparatus for examining particles in a patient's eye according to claim 5; wherein said moveable part of said light projecting means comprises an exit window through which the laser beam is projected toward the patient's eye.

7. An apparatus for examining particles in a patient's eye according to claim 5; wherein said monitoring means comprises visual indicating means for visually indicating the position of the virtual image in relation to the position of the scattered light image.

8. An apparatus for examining particles in a patient's eye according to claim 7; wherein said visual indicating means comprises a light receiving screen.

9. An apparatus for examining particles in a patient's eye according to claim 8; wherein said light receiving screen includes first detecting means for detecting the position of the scattered light image and second detecting means for detecting the position of the virtual image.

10. An apparatus for examining particles in a patient's eye according to claim 7; wherein the visual indicating means comprises a CCD camera for receiving the virtual image and the scattered light image and a monitor screen for displaying the virtual image and the scattered light image.

11. An apparatus for examining particles in a patient's eye according to claim 10; wherein said monitor screen includes first indicating means for indicating a position for the scattered light image and second indicating means for indicating a position for the virtual image.

* * * * *